United States Patent
De Nanteuil et al.

[11] Patent Number: 5,506,237
[45] Date of Patent: Apr. 9, 1996

[54] BICYCLIC NITROGEN COMPOUNDS

[75] Inventors: Guillaume De Nanteuil, Suresnes; Bernard Protevin, Elancourt; Georges Remond, Versailles; Jean Lepagnol, Chaudon; Véronique Heidet, Paris, all of France

[73] Assignee: Adir et Compagnie, Courbevoie, France

[21] Appl. No.: 216,794

[22] Filed: Mar. 23, 1994

[30] Foreign Application Priority Data

Mar. 24, 1993 [FR] France .................. 93 03363

[51] Int. Cl.⁶ .............. A61K 31/435; A61K 31/40
[52] U.S. Cl. .............. 514/299; 514/414; 546/112; 546/146; 546/164; 546/165; 546/201; 546/208; 546/209; 548/188; 548/200; 548/214; 548/215; 548/248; 548/468; 548/518
[58] Field of Search ................. 548/188, 200, 548/214, 215, 248, 468; 546/112, 146, 201, 164, 208, 165, 209; 514/299, 307, 314, 323, 326, 365, 372, 374, 378, 414, 422

[56] References Cited

U.S. PATENT DOCUMENTS

| | | | |
|---|---|---|---|
| 4,826,870 | 5/1989 | Higuchi et al. | 514/422 |
| 4,983,623 | 1/1991 | Henning et al. | 514/414 |
| 5,286,732 | 2/1994 | Vincent et al. | 514/299 |

*Primary Examiner*—Bernard Dentz
*Attorney, Agent, or Firm*—Gordon W. Hueschen

[57] ABSTRACT

The invention relates to the compounds of formula (I):

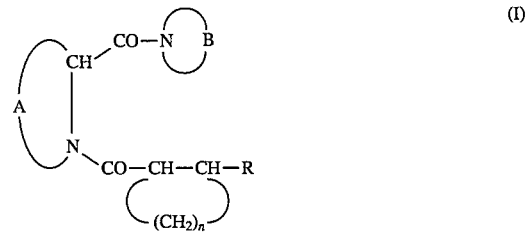

in which:
A represents, with the carbon and nitrogen atoms to which it is attached, a heterocycle,
B represents, with the nitrogen atom to which it is attached, a heterocycle,
n is equal to 1, 2, 3 or 4,
R represents phenyl substituted by at least one halogen or alkyl, hydroxyl, alkoxy, trifluoromethyl, nitro, amino, cyano, carboxyl or alkoxycarbonyl, benzyl, thienyl or pyridyl. The compounds may be used as medicaments.

10 Claims, No Drawings

BICYCLIC NITROGEN COMPOUNDS

The present invention relates to new bicyclic nitrogen compounds.

Aging of the population due to lengthening life spans makes the problem of cerebral aging and of age-related dementias an increasingly significant one. This is why the search for new therapeutic compounds which can counteract memory deficiencies or neuropsychobehavioral disorders of senescence has become a priority.

In addition to the conventional neurotransmitters (acetylcholine, norepinephrine) involved in memory functions, there exist neuropeptides such as vasopressin (AVP) or thyrotropin releasing hormone (TRH) which also exert memory-enhancing effects by playing a neuromodulating role in addition to their peripheral or endocrinal role (Science, 211, 601, 1981).

Recently, studies have shown that the cerebral levels of these peptides decrease significantly in patients affected by senile dementia (Neurobiology, 36, 1133, 1986).

More recently still, it was observed that the activity of prolyl-endopeptidase, a key enzyme in the catabolism of these peptides, greatly increases (+100%) in the brains of sufferers of Alzheimer's disease (Experientia, 46, 94, 1990). This is why it was suggested and demonstrated that inhibitors of prolyl-endopeptidase could counteract memory deficiencies by promoting the memory-enhancing effect of certain neuropeptides and especially of vasopressin. These results were especially observed during experimental amnesia with scopolamine. An excellent correlation between the effect of inhibiting prolyl-endopeptidase and the learning-facilitating effect was reported (EP 321 956) for the inhibiting compounds studied.

It was therefore particularly advantageous to synthesize new compounds having an inhibiting activity towards prolyl-endopeptidase (or post-prolyl cleaving enzyme: PPCE).

The compounds of the present invention, in addition to being new, have been shown to be particularly advantageous by the intensity and duration of their properties in inhibiting prolyl-endopeptidase and thus in preventing the degradation of natural neuropeptides involved in memory functions. Their activity is greater both in vitro and in vivo than that of compounds described in the prior art such as, for example, the compounds described in Patents EP 321,956 and EP 345,428 as PPCE-inhibitors. It is also markedly greater than that of reference nootropes also known for inhibiting the activity of PPCE such as, for example, the compounds described in Patent EP 288,685.

The compounds of the invention are therefore useful for preventing and treating, on the one hand, behavioral disorders, especially of the memory, associated with aging and with acute or chronic neuronal degenerative diseases and, on the other hand, mental disorders associated with anxiety and depression.

The invention more particularly relates to the compounds of general formula (I):

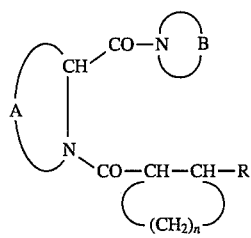

(I)

in which:

A represents, with the carbon and nitrogen atoms to which it is attached, any one of the following heterocycles:

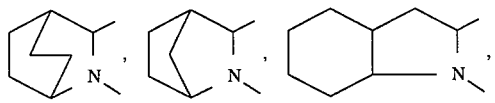

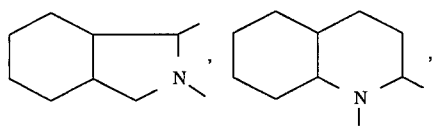

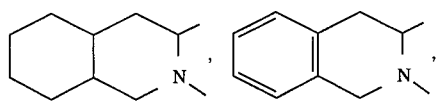

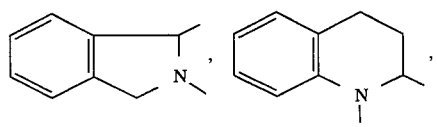

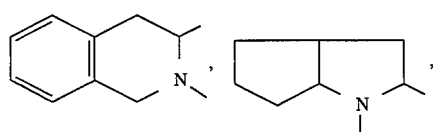

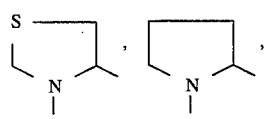

B represents, with the nitrogen atom to which it is attached, any one of the following heterocycles:

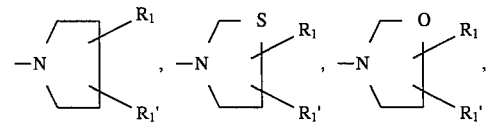

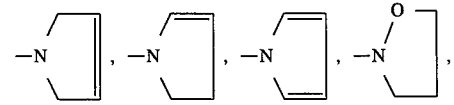

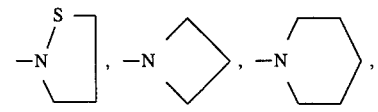

in which $R_1$ or $R_1'$, which are identical or different, represent a hydrogen atom, a linear or branched ($C_1$–$C_6$)alkyl or hydroxyl group or together form an oxo group, n is equal to 1, 2, 3 or 4, R represents:
- a phenyl group substituted by at least one halogen atom or one linear or branched ($C_1$–$C_6$)-alkyl, hydroxyl, linear or branched ($C_1$–$C_6$)-alkoxy, trifluoromethyl, nitro, amino, cyano, carboxyl or linear or branched ($C_1$–$C_6$)alkoxycarbonyl group,
- a benzyl group,
- a thienyl group, or a pyridyl group,
to their enantiomers, diastereoisomers and epimers and to their addition salts with a pharmaceutically acceptable acid.

Mention may be made, among pharmaceutically acceptable acids, in a non-limiting way, of hydrochloric, sulfuric, tartaric, maleic, fumaric, methanesulfonic or camphoric acids and the like.

The invention also applies to the process for the preparation of the compounds of formula (I), wherein an acid of formula (II), the isomers of which have optionally been separated by a conventional separation technique:

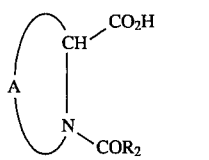   (II)

in which A has the same meaning as in the formula (I) and $R_2$ represents a linear or branched $(C_1–C_6)$alkoxy or benzyloxy group, is reacted with an amine of formula (III) (the isomers of which have optionally been separated by a conventional separation technique):

   (III)

in which B has the same meaning as in the formula (I), according to a peptide coupling technique such as that described by W. Konig and R. Geiger (Ber., 103, 788, 1970) to lead to the compound of formula (IV):

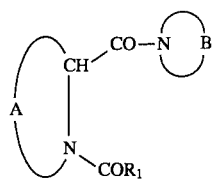   (IV)

in which A, B and $R_1$ have the same meaning as above, which is deprotected by a conventional deprotection technique, to lead to the one of formula (V):

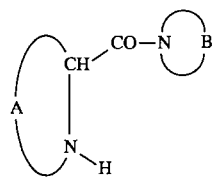   (V)

in which A and B have the same meaning as in the formula (I), which is reacted with an acid of formula (VI), the isomers of which have optionally been separated according to a conventional separation technique:

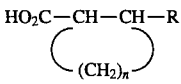   (VI)

in which R and n have the same meaning as in the formula (I), in the presence of a conventional coupling agent for peptide synthesis, to lead to the compound of formula (I) which is purified, if appropriate, by a conventional purification technique, the isomers of which are separated, if desired, by a conventional separation technique and which are converted, if necessary, to its addition salts with a pharmaceutically acceptable acid.

The compounds of formula (I) can also be obtained according to the process, wherein an acid of formula (VII), the isomers of which have optionally been separated by a conventional separation technique:

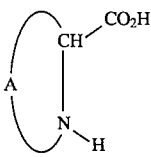   (VII)

in which A has the same meaning as in the formula (I), is reacted with an acid chloride of formula (VIII), the isomers of which have optionally been separated according to a conventional separation technique:

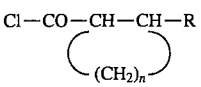   (VIII)

in which R and n have the same meaning as in the formula (I), to lead to the compound of formula (IX):

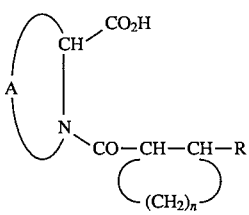   (IX)

in which A, R and n have the same meaning as in the formula (I), which is reacted with an amine of formula (III) (the isomers of which have optionally been separated by a conventional separation technique):

   (III)

in which B has the same meaning as in the formula (I), according to a peptide coupling technique such as that described by W. Konig and R. Geiger (Ber., 103,788, 1970), to lead to the compound of formula (I), which is purified, if appropriate, by a conventional purification technique, the isomers of which are separated, if desired, by a conventional separation technique and which are converted, if necessary, to its addition salts with a pharmaceutically acceptable acid.

Separation of the isomers of the compounds of formula (VI) or (VII) can be carried out according to the technique described in "Optical Resolution for Chemical Compounds" (Vol. 2, Part I/Optical Resolution Information Center, Manhattan College, Riverdale, N.Y. 10471, USA).

The compounds of formula (VI) or (VIII) for which n=1 are obtained in the form of pure enantiomers by stereoselective synthesis according to the technique described by J. Vallgårda et al. (Tet. Lett., 32 (40), 5625–5628, 1991).

The preferred configuration of the compounds of formula (VI) or (VIII) is (R,R).

The compounds of the invention have very advantageous pharmacological properties. They strongly inhibit the activity of prolyl-endopeptidase which makes them useful for the treatment of memory and cognitive disorders and of neurobehavioral disorders associated with aging and with acute or chronic degenerative diseases of the nervous system, such as Alzheimer's disease, Pick's atrophy, Korsakoff's syndrome, cerebrovascular accident, spinal trauma or amyotrophic lateral sclerosis. They are likewise useful in the treatment of mental disorders associated with anxiety and depression.

Another subject of the present invention is pharmaceutical compositions containing, as active principle, at least one compound of general formula (I) or one of its addition salts with a pharmacologically acceptable acid, alone or in combination with one or more inert and nontoxic excipients or vehicles.

Mention may more particularly be made, among pharmaceutical compositions according to the invention, of those which are suitable for oral, parenteral or nasal administration, simple or sugar-coated tablets, sublingual tablets, chartulas, packets, gelatin capsules, glossettes, lozenges, suppositories, creams, ointments, dermal gels, and the like.

The dose varies according to the age and weight of the patient, the nature and the severity of the ailment and on the administration route.

The latter can be oral, nasal, rectal or parenteral. The unit dose generally varies between 0.5 and 100 mg for a treatment taken 1 to 3 times per 24 hours.

The following examples illustrate the invention and do not limit it in any way.

Preparations A to F do not lead to the compounds of the invention but to starting materials which are useful in the preparation of the derivatives of formula (I).

The compounds of Preparations A to E were synthesized according to the technique described by J. Vallgårda et al. (Tet. Lett., 32 (40), 5625–5628, 1991).

Preparation A: (1R,2R)-2-(4-Fluorophenyl)cyclopropanecarboxylic acid

Optical rotation: $[\alpha]_D^{21} = -292.5°$ (c=1%, $CH_2Cl_2$)

| Elemental microanalysis: | C % | H % |
|---|---|---|
| calculated | 66.66 | 5.03 |
| found | 66.57 | 5.02 |

Preparation B: (1R,2R)-2-(2-thienyl)cyclopropanecarboxylic acid
Preparation C: (1R,2R)-2-(3-Trifluoromethylphenyl)-cyclopropane carboxylic acid

| Elemental microanalysis: | C % | H % |
|---|---|---|
| calculated | 57.40 | 3.94 |
| found | 57.21 | 4.49 |

Preparation D: (1R,2R)-2-(4-Methylphenyl)cyclopropanecarboxylic acid
Preparation E: (1R,2R)-2-(4-Methoxyphenyl)cyclopropanecarboxylic acid
Preparation F: cis-2-Benzylcyclopropanecarboxylic acid and trans-2-benzyl cyclopropanecarboxylic acid, The cis and trans isomers of 2-benzylcyclopropanecarboxylic acid were prepared by chromatographic separation of ethyl 2-benzylcyclopropanecarboxylate on a silica column, using a toluene/cyclohexane (90/10) mixture as eluent. This separation is followed by a saponification by sodium hydroxide in ethanolic medium.

EXAMPLE 1

(2S,3aS,7aS)-1-{(1R,2R)-[2-(4-Fluorophenyl-1-cyclopropyl]carbonyl}-2-[(pyrrolidin-1-yl)carbonyl]perhydroindole Stage A: (2S,3aS,7aS)-1-tert-Butyloxycarbonyl-2-[(pyrrolidin-1-yl)carbonyl]perhydroindole The expected product is prepared from pyrrolidine and (2S,3aS,7aS)-1-tert-butyloxycarrbonylperhydroindole-2-carboxylic acid, using the peptide coupling technique (dicyclohexylcarbodiimide/hydroxybenzotriazole-DCC/HOBT) described by W. Konig and R. Geiger (Ber., 103, 788, 1970) and dimethylformamide as solvent, the product being purified by crystallization from ethyl acetate.

Melting point: 149° C.

Stage B: (2S,3aS,7aS)-2-[(Pyrrolidin-1-yl)carbonyl]perhydroindole 30 mmol of the compound described in Stage A are dissolved in 100 ml of ethyl acetate. A stream of hydrochloric acid is passed through the solution while maintaining the temperature at 20° C. and stirring is maintained for 18 hours at room temperature. The solvent is evaporated and the residue is taken up in 100 ml of water. The insoluble material is filtered off and the filtrate, after basifying by addition of sodium bicarbonate, is evaporated to dryness. The residue is finally taken up successively in 100 ml of ethanol, 100 ml of dichloromethane and then 100 ml of ethyl ether. The expected product is obtained after filtration of the salts and evaporation.

Melting point: 83° C.

Stage C: (2S,3aS,7aS)-1-{(1R,2R)-[2-( 4-Fluorophenyl-1-cyclopropyl]carbonyl}[(pyrrolidin-1-yl)carbonyl]perhydroindole The expected product is obtained according to the same process as that described in Stage A, using the compound described in Stage B and the acid described in Preparation A. It is purified by chromatography on a silica column, using a dichloromethane/methanol (97/3) mixture as eluent.

Melting point: 154° C.

Optical rotation: $[\alpha]_D^{22} = -127.5°$ (c=1%, $CH_2Cl_2$)

| Elemental microanalysis: | C % | H % | N % |
|---|---|---|---|
| calculated | 71.85 | 7.60 | 7.29 |
| found | 71.58 | 7.82 | 7.47 |

Examples 2 to 8 were synthesized according to the process described in Example 1, using the corresponding starting materials.

EXAMPLE 2

(3S)-2-{(1R,2R)-[2-(4-Fluorophenyl)-1-cyclopropyl]carbonyl}-3-[(pyrrolidin-1-yl)carbonyl]-2-azabicyclo[2.2.2]octane Melting point: 195° C.

Optical rotation: $[(\alpha]_D^{22} = -132.5$ (c=1%, $CH_2Cl_2$)

| Elemental microanalysis: | C % | H % | N % |
|---|---|---|---|
| calculated | 71.33 | 7.35 | 7.56 |
| found | 70.45 | 7.31 | 7.75 |

EXAMPLE 3

(2S,3aS,7aS)-1-{(1R,2R)-[2-(2-Thienyl)-1-cyclopropyl]carbonyl}-2-[(pyrrolidin-1-yl)carbonyl]perhydroindole Melting point: 157° C.

Optical rotation: $[\alpha]_D^{23} = -125.3°$ (c=1%, $CH_2Cl_2$)

| Elemental microanalysis: | | | | |
|---|---|---|---|---|
| | C % | H % | N % | S % |
| calculated | 67.71 | 7.58 | 7.52 | 8.61 |
| found | 67.26 | 7.61 | 7.72 | 8.47 |

EXAMPLE 4

(3S)-2-{(1R,2R)-[2-(2-Thienyl)-1-cyclopropyl]carbonyl}-3-[(pyrrolidin-1-yl)carbonyl]-2-azabicyclo[2.2.2]octane Melting point: 158° C.

Optical rotation: $[\alpha]_D^{22}$=−130.5° (c=1%, CH$_2$Cl$_2$)

| Elemental microanalysis: | | | | |
|---|---|---|---|---|
| | C % | H % | N % | S % |
| calculated | 67.01 | 7.31 | 7.81 | 8.94 |
| found | 66.34 | 7.39 | 7.85 | 8.70 |

EXAMPLE 5

(2S,3aS,7aS)-1-{(1R,2R)-[2-(3-Trifluoromethylphenyl)-1cyclopropyl]carbonyl}-2-[(pyrrolidin-1-yl)carbonyl]perhydroindole Melting point: 208° C.

Optical rotation: $[\alpha]_D^{22}$=−130.6° (c=1%, CH$_2$Cl$_2$)

| Elemental microanalysis: | | | |
|---|---|---|---|
| | C % | H % | N % |
| calculated | 66.34 | 6.73 | 6.45 |
| found | 66.37 | 6.85 | 6.83 |

EXAMPLE 6

(3S)-2-{(1R,2R)-[2-(3-Trifluoromethylphenyl)-1-cyclopropyl]carbonyl}-3-[(pyrrolidin-1-yl)carbonyl]-2-azabicyclo[2.2.2]octane Melting point: 154° C.

Optical rotation: $[\alpha]_D^{22}$=−129.5° (c=1%, CH$_2$Cl$_2$)

| Elemental microanalysis: | | | |
|---|---|---|---|
| | C % | H % | N % |
| calculated | 65.70 | 6.47 | 6.66 |
| found | 65.52 | 6.25 | 6.74 |

EXAMPLE 7

(2S,3aS,7aS)-1-{(1R,2R )-[2-(4-Methylphenyl)-1-cyclopropyl]carbonyl}-2-[(pyrrolidin-1-yl)carbonyl]perhydroindole Melting point: 142° C.

| Elemental microanalysis: | | | |
|---|---|---|---|
| | C % | H % | N % |
| calculated | 75.75 | 8.48 | 7.36 |
| found | 74.42 | 8.62 | 7.36 |

EXAMPLE 8

(3S)-2-{(1R,2R)-[2-(4-Methoxyphenyl)-1-cyclopropyl]carbonyl}-3-[(pyrrolidin-1-yl)carbonyl]-2-azabicyclo[2.2.2]octane Melting point: 212° C.

| Elemental microanalysis: | | | |
|---|---|---|---|
| | C % | H % | N % |
| calculated | 72.22 | 7.91 | 7.32 |
| found | 71.60 | 7.90 | 7.21 |

EXAMPLE 9

(3S)-2-[trans-(2-Benzyl-1-cyclopropyl)carbonyl]-3-[(pyrrolidin-1-yl)carbonyl]-2-azabicyclo[2.2.2]octane, α isomer and

EXAMPLE 10

(3S)-2-[trans-(2-Benzyl-1-cyclopropyl)carbonyl]-3-[(pyrrolidin-1-yl)carbonyl]-2-azabicyclo[2.2.2]octane, β isomer The α and β isomers were separated by chromatography on a silica column, using a dichloromethane/ethyl acetate (50/50) mixture as eluent.

EXAMPLE 9

Optical rotation: $[\alpha]_D^{22}$=+27.9° (c=1%, CH$_2$Cl$_2$)

| Elemental microanalysis: | | | |
|---|---|---|---|
| | C % | H % | N % |
| calculated | 75.38 | 8.25 | 7.64 |
| found | 75.45 | 8.61 | 7.31 |

EXAMPLE 10

Optical rotation: $[\alpha]_D^{22}$=−28.2° (c=1%, CH$_2$Cl$_2$)

| Elemental microanalysis: | | | |
|---|---|---|---|
| | C % | H % | N % |
| calculated | 75.38 | 8.25 | 7.64 |
| found | 75.41 | 8.44 | 7.52 |

EXAMPLE 11

(2S,3aS,7aS)-1-[cis-(2-Benzyl-1-cyclopropyl)carbonyl]- 2-[(pyrrolidin-1-yl)carbonyl]perhydroindole, α isomer and

EXAMPLE 12

(2S,3aS,7aS)-1-[cis-(2-Benzyl-1-cyclopropyl)carbonyl]- 2-[(pyrrolidin-1-yl)carbonyl]perhydroindole, β isomer The α and β isomers were separated by chromatography on a silica column, using a dichloromethane/ethyl acetate (95/5) mixture as eluent.

EXAMPLE 11

Melting point: 145° C.
Optical rotation: $[\alpha]_D^{22} = -47.3°$ (c=1%, $CH_2Cl_2$)

Elemental microanalysis:

|  | C % | H % | N % |
|---|---|---|---|
| calculated | 75.75 | 8.48 | 7.36 |
| found | 75.95 | 8.24 | 6.98 |

EXAMPLE 12

Oil
Optical rotation: $[\alpha]_D^{22} = -21.6°$ (c=1%, $CH_2Cl_2$)

Elemental microanalysis:

|  | C % | H % | N % |
|---|---|---|---|
| calculated | 75.75 | 8.48 | 7.36 |
| found | 75.14 | 8.18 | 7.20 |

EXAMPLE 13

(2S,3aS,7aS)-1-[trans-(2-Benzyl-1-cyclopropyl)carbonyl]-2-[(pyrrolidin-1-yl)carbonyl]perhydroindole, α isomer and

EXAMPLE 14

(2S,3aS,7aS)-1-[trans-(2-Benzyl-1-cyclopropyl)carbonyl]-2-[(pyrrolidin-1-yl)carbonyl]perhydroindole, β isomer The α and β isomers were separated by chromatography on a silica column, using a dichloromethane/ethyl acetate (50/50) mixture as eluent.

EXAMPLE 13

Oil
Optical rotation: $[\alpha]_D^{22} = +37.5°$ (c=1%, $CH_2Cl_2$)

Elemental microanalysis:

|  | C % | H % | N % |
|---|---|---|---|
| calculated | 75.75 | 8.48 | 7.36 |
| found | 75.37 | 8.94 | 6.93 |

EXAMPLE 14

Oil
Optical rotation: $[\alpha]_D^{22} = -14.2°$ (c=1%, $CH_2Cl_2$)

Elemental microanalysis:

|  | C % | H % | N % |
|---|---|---|---|
| calculated | 75.75 | 8.48 | 7.36 |
| found | 75.28 | 8.46 | 7.34 |

Pharmacologicial Study of the Derivatives of the Invention

EXAMPLE 15

Measurement of the anti-prolyl-endopeptidase activity

The method of Yoshimoto and Tsuru (Agr. Biol. Chem., 42, 2417, 1978) was used. Prolyl-endopeptidase was isolated from Flavobacterium meningosepticum. The enzymatic substrate is Z-Gly-Pro-pNitroaniline.

A mixture of 0.1M phosphate buffer (pH 7; 0.99 ml), of 2M substrate (0.25 ml) and of a solution of the inhibiting compound to be tested (0.01 ml) is incubated at 37° C. for 5 minutes. 0.1 ml of a prolyl-endopeptidase solution (0.5 U/ml) is then added and the mixture is left for 10 minutes at 37° C. The enzymatic reaction is halted by addition of 2 ml of a 1M acetate buffer/Triton X-100 solution (pH 4). After standing at room temperature, the absorbence is measured at 410 nm.

A control measurement is carried out by replacing the solution of the compound to be tested by tile same volume of phosphate buffer. The percentage of inhibition of the enzyme is calculated from this control measurement. The concentration which inhibits prolyl-endopepotidase by 50 % ($IC_{50}$) is determined for each compound tested.

The compounds of the invention were compared with two reference compounds known for their high inhibiting activity towards prolyl-endopeptidase and initially described for this purpose: (S)-1-[N-4-chlorobenzylsuccinamoyl] pyrrolidine-2-carbaldehyde (EP 345,428), known below as ONO, and N-(4-phenylbutanoyl)-L-thiaprolylpyrrolidineimide (Example 3: EP 321,956), known below as Zeria.

The derivatives of the invention exert a high inhibiting activity on prolyl-endopeptidase which is greater than that of the reference compounds, as shown in the table of the $IC_{50}$ values:

| Zeria | $5.4 \cdot 10^{-7}$ M |
|---|---|
| ONO | $5.7 \cdot 10^{-7}$ M |
| Example 1 | $1.4 \cdot 10^{-8}$ M |

| | |
|---|---|
| Example 2 | $4.10^{-8}$M |
| Example 3 | $1.4.10^{-8}$M |
| Example 6 | $3.0.10^{-9}$M |

EXAMPLE 16

Inhibition of prolyl-endopeptidase

Measurement of the inhibition of prolyl-endopeptidase was carried out in vitro and in vivo in rat cerebral cortex, by virtue of a substrate closely related to a peptide naturally cleaved by prolyl-endopeptidase, thyrotropin releasing hormone (TRH).

A cerebral cortex extract is prepared by milling the tissue in a phosphate buffer (25 mM $NaH_2PO_4$, 2 mM DTT, 0.5 mM EDTA-2K) in the proportion of 5 ml/g.

After centrifuging, 200 l of supernatant are incubated for 15 minutes at 37° C. in a final volume of 2.1 ml to which 250 l of substrate (TRH-pNitroaniline) are added for a further incubation of 20 minutes followed by immediately reading the absorbence at 410 nm.

The tested product is either added to the cortex extract before the first incubation (determination of in vitro $IC_{50}$) or administered by the IP route 30 minutes before the preparation of the tissue extract.

Under the test conditions, the compounds of the invention strongly inhibit prolyl-endopeptidase in rat cerebral cortex both in vitro and after in vivo administration. This activity is yet again much greater than that of the reference compounds.

| | in vitro $IC_{50}$ | in vivo Inhibition dose (mg/kg) | % |
|---|---|---|---|
| Zeria | $5.4.10^{-8}$M | 30 | 47 |
| | | 10 | 16 |
| ONO | $5.7.10^{-8}$M | 30 | 19 |
| | | 10 | 5 |
| Example 1 | $1.1.10^{-9}$M | 1 | 54 |
| Example 2 | $4.10^{-9}$M | 1 | 42 |
| Example 3 | $1.4.10^{-9}$M | 1 | 59 |
| Example 4 | $4.8.10^{-9}$M | 3 | 23 |
| Example 5 | $1.10^{-9}$M | 1 | 58 |
| Example 6 | $3.2.10^{-9}$M | 1 | 49 |
| Example 14 | $2.5.10^{-9}$M | 1 | 41 |

EXAMPLE 17

Duration of action

The duration of action of the compounds with respect to in vivo inhibition of prolyl-endopeptidase in rat cerebral cortex was estimated according to the same methodology as in Example 16, by administering the studied compounds by the IP route at various times before preparation of the tissue extract. The time for which the inhibiting effect is equal to 50 % of the maximum effect (measured at 30 minutes) was calculated ($t_{1/2}$).

The oral bioavailability of the compounds of the invention was likewise estimated by administering them by the IP or oral route 30 minutes or 60 minutes before measuring the inhibiting effect. The oral bioavailability index (OBI) was determined by dividing the inhibiting effect (%) measured after oral administration by that measured after IP administration. The most active compounds of the invention exert their effect according to a cerebral duration of action which is much longer than that of the reference compounds and with a much greater oral bioavailability, which gives them a preponderant therapeutic advantage.

| | dose (mg/kg) | $t_{1/2}$ | OBI |
|---|---|---|---|
| Zeria | 30 | 1 hour | 0.30 |
| ONO | 30 | 1 hour | <0.30 |
| Example 1 | 1 | 7 hours | 0.90 |
| Example 2 | 1 | 7 hours | 0.78 |
| Example 6 | 1 | 3 hours | 0.43 |

Pharmaceutical Composition

EXAMPLE 18

Tablet: Formula for the preparation of 1000 tablets each containing a dose of 10 mg

| | |
|---|---|
| Compound of Example 1 | 10 g |
| Hydroxypropyl cellulose | 2 g |
| Wheat starch | 10 g |
| Lactose | 100 g |
| Magnesium stearate | 3 g |
| Talc | 3 g |

What is claimed is:

1. A compound selected from those of formula (I):

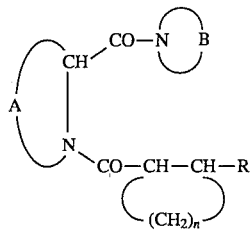

(I)

in which:

A represents, with the carbon and nitrogen atoms to which it is attached, any one of the following heterocycles:

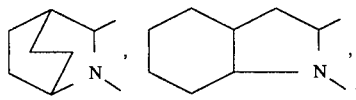

B represents, with the nitrogen atom to which it is attached, any one of the following heterocycle:

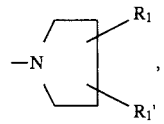

in which $R_1$ or $R_1'$, which are identical or different, represent hydrogen, linear or branched ($C_1$-$C_6$)alkyl or hydroxyl or together form an oxo group, n is equal to 1, 2, 3 or 4, R represents:

a phenyl group substituted by at least one halogen hydroxyl, linear or branched ($C_1$-$C_6$)alkoxy, trifluoromethyl, nitro, amino, cyano, carboxyl or linear or branched ($C_1$-$C_6$)alkoxycarbonyl, its enantiomers, diastereoisomers and epimers and its addition salts with a pharmaceutically acceptable acid.

2. A compound of claim 1, selected from those wherein A represents, with the carbon and nitrogen atoms to which it is attached, a 2-azabicyclo[2.2.2]octane ring, its enantiomers, diasteroisomers and epimers and its addition salts with a pharmaceutically-acceptable acid.

3. A compound of claim 1, selected from those wherein A represents, with the carbon and nitrogen atoms to which it is attached, a perhydroindole ring, its enantiomers, diastereoisomers and epimers and its addition salts with a pharmaceutically-acceptable acid.

4. A compound of claim 1, selected from those wherein B represents, with the nitrogen atom to which it is attached, a pyrrolidine ring, its enantiomers, diastereoisomers and epimers and its addition salts with a pharmaceutically-acceptable acid.

5. A compound of claim 1, selected from those wherein R represents phenyl substituted by at least one halogen, hydroxyl, linear or branched $(C_1-C_6)$alkoxy, trifluoromethyl, nitro, amino, cyano, carboxyl or linear or branched $(C_1-C_6)$alkoxycarbonyl, its enantiomers, diastereoisomers and epimers and its addition salts with a pharmaceutically-acceptable acid.

6. A compound of in claim 1, which is (2S,3aS,7aS)-1-{(1R,2R)-[2-(4-fluorophenyl)-1-cyclopropyl]carbonyl}-2-[(pyrrolidin-1-yl)carbonyl]perhydroindole.

7. A compound of formula (I) as claimed in claim 1, which is (3S)-2-{(1R,2R)-[2-(4-fluorophenyl)-1-cyclopropyl]carbonyl}- 3-[(pyrrolidin-1yl)carbnyl] 2-azabicyclo[2.2.2]octane.

8. A compound of formula (I) as claimed in claim 1, which is (3S)-2-{(1R,2R)-[2-(3-trifluoromethylphenyl)-1-cyclopropyl]carbonyl}-3-[(pyrrolidin-1-yl)carbonyl]- 2-azabicyclo[2.2.2]octane.

9. A method for treating a mammal afflicted with a condition requiring a prolylendopeptidase inhibitor comprising the step of administering to the mammal an amount of a compound of claim 1 which is effective for alleviation of said conditions.

10. A pharmaceutical composition useful as a prolylendopeptidase inhibitor comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,506,237            Page 1 of 4
DATED : April 9, 1996
INVENTOR(S) : Guillaume De Nanteuil, Bernard Portevin, Georges Remond, Jean Lapagnol, Veronique Heidet It is certified that error appears in the above-indentified patent and that said Letters Patent is hereby corrected as shown below:

Title Page, [75] Inventors: "Protevin" should read -- Portevin --. See Declaration.

Column 2, line 16: Seventh (7th) formula is incorrect. Correct formula is:

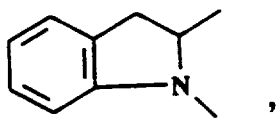

Column 2, line 43: All "$R_1'$" should read -- $R'_1$ --.

Column 2, line 54: "$R_1$," should read -- $R'_1$ --.

Column 4, line 45: "(VII)" should read -- (VIII) --

Column 5, line 59: "(2S,3aS,7aS)-1-{" should read -- (2S,3aS,7aS)-1-{(1R,2R)- --.

Column 5, line 60: Delete "1R,2R)-" from beginning of the line.

UNITED STATES PATENT AND TRADEMARK OFFICE
CERTIFICATE OF CORRECTION

PATENT NO. : 5,506,237
DATED : April 9, 1996
INVENTOR(S) : Guillaume De Nanteuil, Bernard Portevin, Georges Remond, Jean Lapagnol, Veronique Heidet It is certified that error appears in the above-indentified patent and that said Letters Patent is hereby corrected as shown below:

Column 5, line 66: "carrbonylperhydroindole-2-" should read -- carbonylperhydroindole-2- --.

Column 6, line 21: "1-cyclopropyl]carbonyl}" should read -- 1-cyclopropyl]carbonyl}-2- --.

Column 6, line 45: Delete the "(" at the end of the line.

Column 6, line 46: Add "(" to beginning of the line.

Column 6, line 62: Add -- 1R,2R)- -- to end of the line.

Column 6, line 63: Delete "1R,2R)-" from the beginning of the line.

Column 7, line 34: "1cyclopropyl]" should read -- 1-cyclopropyl] --.

Column 8, line 3: Add -- 2- -- to end of the line.

Column 8, line 4: Delete "2-" from beginning of the line

Column 8, line 17: Add -- 2- -- to the end of the line.

UNITED STATES PATENT AND TRADEMARK OFFICE
CERTIFICATE OF CORRECTION

PATENT NO. : 5,506,237

DATED : April 9, 1996

INVENTOR(S) : Guillaume De Nanteuil, Bernard Portevin, Georges Remond, Jean Lapagnol, Veronique Heidet It is certified that error appears in the above-indentified patent and that said Letters Patent is hereby corrected as shown below:

Column 8, line 18: Delete "2-" from beginning of the line.

Column 10, line 46: "tile" should read -- the --. Pg. 12, line 11.

Column 10, line 49: "endopepotidase" should read -- endopeptidase --.

Column 12, line 57: "$R_1$'" should read -- $R'_1$ --.

Column 12, line 58: "or $R_1$." should read -- and $R'_1$ --.

Column 13, line 2: Add a -- - -- (hyphen) after "pharmaceutically".

Column 13, line 21: Add a -- , -- (comma) after "carboxyl".

UNITED STATES PATENT AND TRADEMARK OFFICE
CERTIFICATE OF CORRECTION

PATENT NO. 5,506,237

DATED : April 9, 1996

INVENTOR(S): Guillaume De Nanteuil, Bernard Portevin, Georges Remond, Jean Lapagnol, Veronique Heidet It is certified that error appears in the above-indentified patent and that said Letters Patent is hereby corrected as shown below:

Column 14, line 1: Delete "in".

Column 14, line 4: Delete "formula (1) as claimed in". Pg. 2 of P.A. dtd 3/23/94, Column 14, line 6: "bonyl}- 3-[(pyrrolidin-1ylcarbnyl] 2-azabicyclo[2.2.2]oc-" should read -- bonyl}-3-[(pyrrolidin-1-yl)carbonyl]-2-azabicyclo[2.2.2]oc-".

Column 14, line 8: Delete "formula (1) as claimed in".

Signed and Sealed this

Sixth Day of August, 1996

Attest:

BRUCE LEHMAN

Attesting Officer

Commissioner of Patents and Trademarks